United States Patent
Glenn, Jr. et al.

(10) Patent No.: US 9,198,838 B2
(45) Date of Patent: *Dec. 1, 2015

(54) POROUS, DISSOLVABLE SOLID SUBSTRATE AND SURFACE RESIDENT COATING COMPRISING WATER SENSITIVE ACTIVES

(75) Inventors: Robert Wayne Glenn, Jr., Liberty, OH (US); Kathleen Mary Kaufman, Cincinnati, OH (US); James Charles Dunbar, Morrow, OH (US); John Michael Gardlik, Cincinnati, OH (US); Bryan Patrick Murphy, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/962,888

(22) Filed: Dec. 8, 2010

(65) Prior Publication Data

US 2011/0195098 A1 Aug. 11, 2011

Related U.S. Application Data

(60) Provisional application No. 61/267,698, filed on Dec. 8, 2009.

(51) Int. Cl.

| | |
|---|---|
| *A61K 8/02* | (2006.01) |
| *A61K 8/34* | (2006.01) |
| *A61K 8/46* | (2006.01) |
| *A61K 8/81* | (2006.01) |
| *A61Q 5/02* | (2006.01) |
| *A61Q 5/08* | (2006.01) |
| *A61Q 19/10* | (2006.01) |

(52) U.S. Cl.
CPC .............. *A61K 8/02* (2013.01); *A61K 8/0216* (2013.01); *A61K 8/345* (2013.01); *A61K 8/463* (2013.01); *A61K 8/8129* (2013.01); *A61Q 5/02* (2013.01); *A61Q 5/08* (2013.01); *A61Q 19/10* (2013.01)

(58) Field of Classification Search
CPC combination set(s) only.
See application file for complete search history.

(56) References Cited

U.S. PATENT DOCUMENTS

| | | | |
|---|---|---|---|
| 2,356,168 | A | 8/1941 | Mabley |
| 4,149,551 | A | 4/1979 | Benjamin et al. |
| 4,206,196 | A | 6/1980 | Davis |
| 5,261,426 | A | 11/1993 | Kellett et al. |
| 5,976,454 | A | 11/1999 | Sterzel et al. |
| 6,106,849 | A * | 8/2000 | Malkan et al. ............ 424/401 |
| 6,365,142 | B1 | 4/2002 | Tamura |
| 6,525,034 | B2 | 2/2003 | Dalrymple et al. |
| 6,800,295 | B2 | 10/2004 | Fox |
| 6,808,375 | B2 | 10/2004 | Klotzer |
| 6,825,161 | B2 | 11/2004 | Shefer et al. |
| 6,831,046 | B2 | 12/2004 | Carew et al. |
| 7,208,460 | B2 | 4/2007 | Shefer et al. |
| 7,387,787 | B2 | 6/2008 | Fox |
| 8,197,830 | B2 | 6/2012 | Helfman et al. |
| 8,268,764 | B2 | 9/2012 | Glenn, Jr. et al. |
| 8,273,333 | B2 | 9/2012 | Glenn et al. |
| 8,288,332 | B2 | 10/2012 | Fossum et al. |
| 8,309,505 | B2 | 11/2012 | Fossum et al. |
| 8,349,341 | B2 | 1/2013 | Glenn, Jr. et al. |
| 8,349,786 | B2 | 1/2013 | Glenn et al. |
| 8,349,787 | B2 | 1/2013 | Glenn et al. |
| 8,415,287 | B2 | 4/2013 | Glenn, Jr. et al. |
| 8,461,090 | B2 | 6/2013 | Glenn, Jr. et al. |
| 8,461,091 | B2 | 6/2013 | Glenn, Jr. et al. |
| 8,466,099 | B2 | 6/2013 | Glenn, Jr. et al. |
| 8,476,211 | B2 | 7/2013 | Glenn, Jr. et al. |
| 8,546,640 | B2 | 10/2013 | Popovsky et al. |
| 2002/0064510 | A1 | 5/2002 | Dalrymple |
| 2003/0209166 | A1 | 11/2003 | Vanmaele et al. |
| 2004/0202632 | A1 * | 10/2004 | Gott et al. ............... 424/70.13 |
| 2004/0242097 | A1 | 12/2004 | Hasenoehrl et al. |
| 2005/0136098 | A1 * | 6/2005 | Spadini et al. ............ 424/443 |
| 2008/0083420 | A1 | 4/2008 | Glenn et al. |
| 2008/0292669 | A1 | 11/2008 | Deng et al. |
| 2011/0027328 | A1 | 2/2011 | Baig et al. |
| 2011/0195098 | A1 | 8/2011 | Glenn, Jr. et al. |
| 2012/0270029 | A1 | 10/2012 | Granberg et al. |
| 2012/0321580 | A1 | 12/2012 | Glenn, Jr. et al. |
| 2013/0236520 | A1 | 9/2013 | Popovsky et al. |

FOREIGN PATENT DOCUMENTS

| | | |
|---|---|---|
| EP | 1958532 A2 | 8/2008 |
| JP | 62-081432 | 4/1987 |
| JP | 07-53349 | 2/1995 |
| JP | 10251371 A1 | 9/1998 |
| WO | 01/19948 A1 | 3/2001 |
| WO | 01/25322 A1 | 4/2001 |
| WO | 01/25393 A1 | 4/2001 |
| WO | 2004/041991 A1 | 5/2004 |

OTHER PUBLICATIONS

U.S. Appl. No. 13/440,475, filed Apr. 5, 2012, Glenn, Jr.
PCT International Search Report and Written Opinion dated Jun. 7, 2013.
P&G Case 12068M dated Jul. 20, 2012, PCT/US2012/032253, 5 pages.
P&G Case 11787 ISR dated Feb. 20, 2013, PCT/US2011/042640, 12 pages.

* cited by examiner

*Primary Examiner* — Michael G Hartley
*Assistant Examiner* — Robert Cabral
(74) *Attorney, Agent, or Firm* — Angela K. Haughey

(57) ABSTRACT

The present invention relates to personal care compositions, especially those personal care compositions in the form of a personal care article that is a porous dissolvable solid substrate. The porous dissolvable solid substrate has a surface resident coating comprising a water sensitive active that can deliver a consumer benefit.

25 Claims, 3 Drawing Sheets

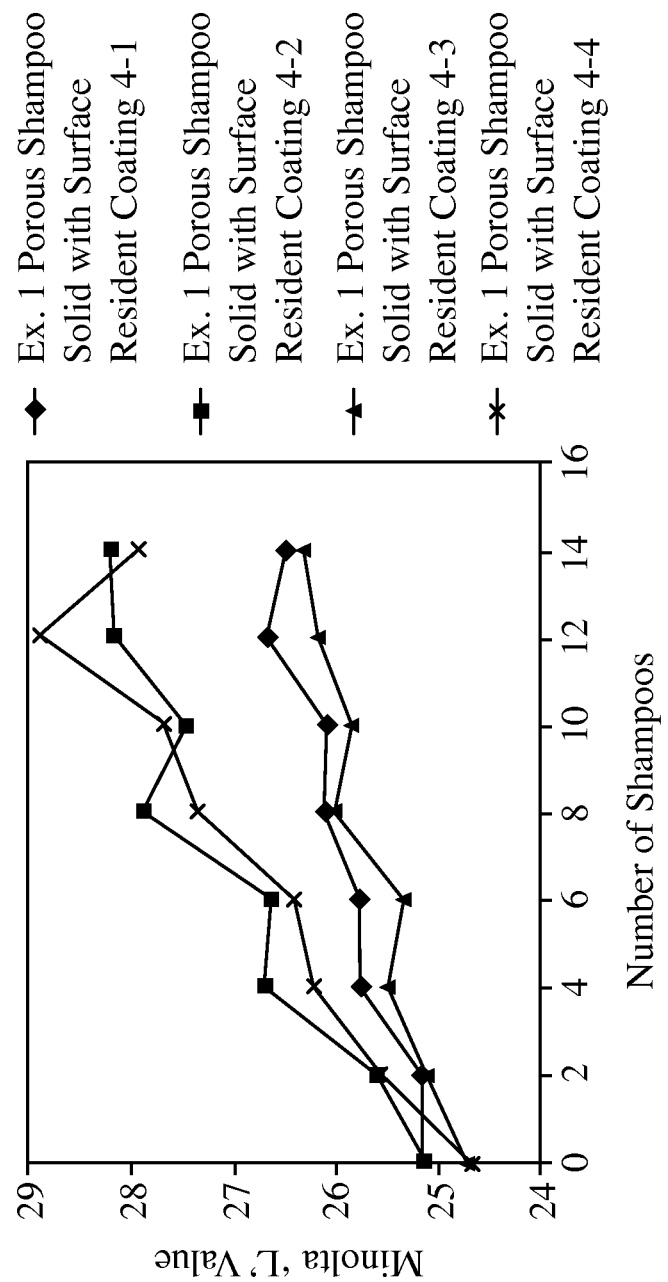

POROUS, DISSOLVABLE SOLID SUBSTRATE AND SURFACE RESIDENT COATING COMPRISING WATER SENSITIVE ACTIVES

CROSS REFERENCE TO RELATED APPLICATION

This application claims the benefit of U.S. Provisional Application Ser. No. 61/267,698 filed Dec. 8, 2010.

FIELD OF THE INVENTION

The present invention relates to personal care compositions, especially those personal care compositions providing personal care benefits in the form of an article comprising a porous dissolvable solid substrate and surface resident coating comprising water sensitive actives.

BACKGROUND OF THE INVENTION

Personal care compositions have traditionally been sold as liquid products. These liquid personal care products typically comprise a substantial amount of water in the formula. Traditionally it has been difficult to include water sensitive actives which are chemically incompatible or hydrolytically sensitive, due to the nature of the aqueous environment of the liquid product. By eliminating the aqueous environment (the solvent), the personal care products of the present invention have improved shelf stability of water sensitive chemically incompatible and hydrolytically sensitive actives. During usage, the consumer adds water to the personal care product, which activates the water sensitive actives to deliver their consumer desirable benefit at the desired point of time of product application.

Additionally, the personal care product of the present invention expands the number and type of cosmetic actives that can be employed by the formulator and enables the delivery of new consumer benefits which have previously been difficult to achieve without dual compartment packaging or by the consumer having to mix differing compositions in a multi-step process. Such consumer benefits are "water activated" and include, but are not limited to, self-lathering (effervescence), self-warming, gradual hair lightening/blonding, gradual hair coloring, and visual color change of the product.

SUMMARY OF THE INVENTION

The present invention meets the aforementioned needs. The present invention provides a porous dissolvable solid substrate in the form of a unit dose personal care article that can be conveniently and quickly dissolved in the palm of the consumer's hand to reconstitute a liquid personal care composition for ease of application to hair while providing the consumer with new benefits enabled by the incorporation of water sensitive actives.

A personal care article comprising: a porous dissolvable solid substrate comprising (i) from about 10% to about 75% of a surfactant, (ii) from about 10% to about 50% water-soluble polymer, (iii) from about 1% to about 30% plasticizer; and a surface resident coating comprising from about 10% to about 100% of one or more water sensitive actives, wherein the ratio of the porous dissolvable solid substrate to the surface resident coating is from about 110:1 to about 0.1:1.

A method for making a personal care article, the method comprising applying a surface resident coating comprising the water sensitive active in powdered form to a porous dissolvable solid substrate comprising from about 10% to about 75% of a surfactant, from about 10% to about 50% water-soluble polymer, and from about 1% to about 30% plasticizer.

A method for making a personal care article, the method comprising: preparing a processing mixture comprising from about 5% to about 50% of a surfactant, from about 5% to about 35% water-soluble polymer, and from about 0.5% to about 20% plasticizer; aerating the processing mixture by introducing a gas into the processing mixture to form an aerated wet mixture; forming the aerated wet mixture into one or more desired shapes; drying the aerated wet mixture to form a porous dissolvable solid substrate; and applying a surface resident coating comprising the water sensitive active in powdered form to the porous dissolvable solid substrate.

BRIEF DESCRIPTION OF THE DRAWINGS

While the specification concludes with claims which particularly point out and distinctly claim the present invention, it is believed that the present invention will be better understood from the following description of embodiments, taken in conjunction with the accompanying drawings, in which like reference numerals identify identical elements and wherein:

FIG. 5 is a graph depicting L-values.

DETAILED DESCRIPTION OF THE INVENTION

Figure 1:
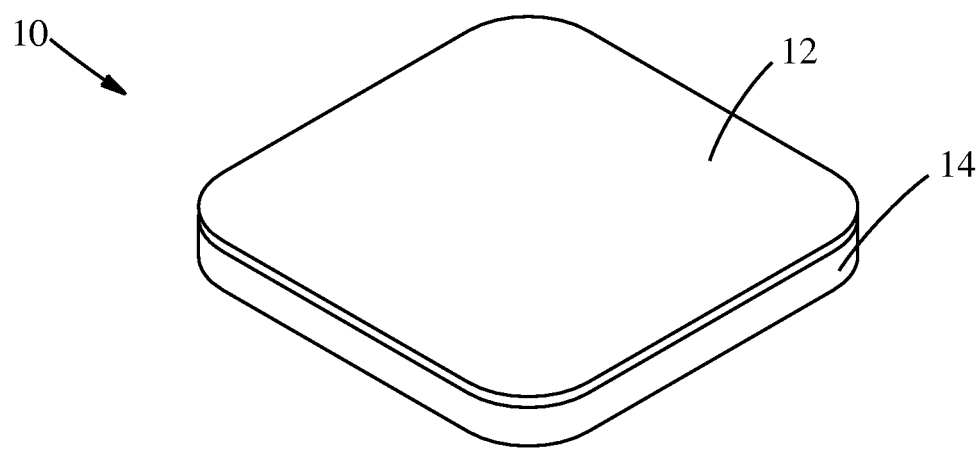
FIG. 1 is a schematic view of a porous dissolvable solid substrate with a surface resident coating comprising a water sensitive active.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

I. Definitions

As used herein, the term "personal care composition" means a composition that may be applied to mammalian hair and skin without undue undesirable effects.

As used herein, the term "surface resident coating comprising a water sensitive active" refers to a surface resident powder coating comprising the water sensitive active that is adsorbed to at least a portion of the solid/air interface of the porous dissolvable solid substrate. The resulting surface resident coating minimizes the physical interactions between the water sensitive active and the bulk of the dissolvable porous solid both during the manufacture and over the shelf life of the product, and before the personal care article is put in contact with water during consumer use.

As used herein, the term, "surface resident coating" refers to a coating which is adsorbed to at least a portion of the solid/air interface of the porous dissolvable solid substrate.

As used herein, "personal care article" means the porous dissolvable solid substrate comprising a surfactant, water-soluble polymer, and plasticizer, along with the surface resident coating. The personal care article may be referred to herein as "the article."

As used herein, "dissolvable" means that the porous dissolvable solid substrate has a dissolution rate that satisfies the Hand Dissolution Method Test described herein.

As used herein "porous dissolvable solid substrate" means a solid polymer-containing matrix that defines an interconnected network of spaces or cells that contain the gas of the surrounding atmosphere, typically air. The interconnectivity of the structure may be described by a Star Volume, a Structure Model Index (SMI) or a Percent Open Cell Content.

II. Personal Care Article

The personal care article of the present invention delivers is capable of delivering new benefits to the consumer from a lathering/cleansing product by enabling the delivery of water sensitive actives which previously had been difficult to incorporate, as the water sensitive actives are generally unstable in the presence of the water traditionally included in personal care products.

This is achieved by incorporating the water sensitive actives as a surface resident coating on the porous dissolvable solid substrate rather than trying to incorporate the water sensitive active within the porous dissolvable solid substrate during the making process. Any suitable application method can be used to apply the surface resident coating comprising the water sensitive active to the porous dissolvable solid substrate to form a surface resident coating that is adsorbed to at least a portion of the solid/air interface of the porous dissolvable solid substrate. In a one embodiment the surface resident coating comprising the water sensitive active is in the form of a powder coating, which is applied to the surface of the porous dissolvable solid substrate. Traditionally, when water sensitive actives and water are combined together in a composition the water sensitive active does not remain stable (i.e. the water sensitive active either degrades or decomposes or inactivates either during the production process or during the shelf life of the product). Thus when the consumer uses the personal care product the water sensitive active no longer has its intended activity. While this may still occur in the present inventive personal care articles as they are dissolved in water immediately prior to application, the target substrate (i.e. the hair and/or skin) is present when the water sensitive active is first contacted with the water (solvent) and the consumer has a greater opportunity for the water sensitive active to have its intended effect.

A. The Porous Dissolvable Solid Substrate

The porous dissolvable solid substrate comprises a surfactant, a water-soluble polymer, and a plasticizer. The porous dissolvable solid substrate can be prepared such that it can be conveniently and quickly dissolved in the palm of the consumer resulting in a liquid personal care composition. Once dissolved, this personal care composition can be used in a manner similar to conventional liquid personal care compositions, i.e. applied to the scalp and/or hair. The porous dissolvable solid substrate has a maximum Cell Wall Thickness. The porous dissolvable solid substrate has a Cell Wall Thickness of from about from about 0.02 mm to about 0.15 mm, in one embodiment from about 0.025 mm to about 0.12 mm, in another embodiment from about 0.03 mm to about 0.09 mm, and in still another embodiment from about 0.035 mm to about 0.06 mm. The porous dissolvable solid substrate has a minimum level of interconnectivity between the cells, which is quantified by the Star Volume, the Structure Model Index (SMI), and the Percent Open Cell Content. The porous dissolvable solid substrate has a Star Volume of from about 1 $mm^3$ to about 90 $mm^3$, in one embodiment from about 1.5 $mm^3$ to about 60 $mm^3$, in another embodiment from about 2 $mm^3$ to about 30 $mm^3$, and in still another embodiment from about 2.5 $mm^3$ to about 15 $mm^3$. The porous dissolvable solid substrate has a non-negative Structure Model Index of from about 0.0 to about 3.0, in one embodiment from about 0.5 to about 2.75, and in another embodiment from about 1.0 to about 2.50. The porous dissolvable solid substrate has a Percent Open Cell Content of from about 80% to 100%, in one embodiment from about 85% to about 97.5%, and in another embodiment from about 90% to about 95%. The porous dissolvable solid substrate also has a minimum Specific Surface Area. The porous dissolvable solid substrate has a specific surface area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$. The porous dissolvable solid substrate has a basis weight of from about 125 grams/$m^2$ to about 3,000 grams/$m^2$, in one embodiment from about 300 grams/$m^2$ to about 2,500 grams/$m^2$, in another embodiment from about 400 grams/$m^2$ to about 2,000 grams/$m^2$, in another embodiment from about 500 grams/$m^2$ to about 1,500 grams/$m^2$ and in another embodiment from about 600 grams/$m^2$ to about 1,200 grams/$m^2$, and in another embodiment from about 700 to about 1,000 grams/$m^2$ The porous dissolvable solid substrate has a solid density of from about 0.03 $g/cm^3$ to about 0.40 $g/cm^3$, in one embodiment from about 0.05 $g/cm^3$ to about 0.35 $g/cm^3$, in another embodiment from about 0.08 $g/cm^3$ to about 0.30 $g/cm^3$, in another embodiment from about 0.10 $g/cm^3$ to about 0.25 $g/cm^3$, and in another embodiment from about 0.12 $g/cm^3$ to about 0.20 $g/cm^3$.

In one embodiment, the porous dissolvable solid substrate of present invention is a flat, flexible substrate in the form of a pad, a strip or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology. In another embodiment, the porous dissolvable solid substrate of the present invention can also take the form of a dissolvable fibrous web structure.

1. Surfactants

The porous dissolvable solid substrates of the present invention may be lathering or non-lathering under consumer relevant usage instructions. The porous dissolvable substrates include at least one surfactant as a processing aid to generate a stable foam solid prior to drying (solidification) and in the case of a lathering substrate the surfactant may also serve dual functions as a foaming and/or cleansing agent.

a. Lathering Porous Dissolvable Solid Substrates

Lathering porous dissolvable solid substrates for the purposes of lathering and/or cleaning comprise from about 10% to about 75%, in one embodiment from about 30% to about 70%, and in another embodiment from about 40% to about 65% by weight of the personal care article of surfactant;

wherein the surfactant comprises one or more surfactants from Group I, wherein Group I includes anionic surfactants which are suitable for use in hair care or other personal care compositions, and optionally one or more surfactants from Group II, wherein Group II includes a surfactant selected from the group consisting of amphoteric, zwitterionic and combinations thereof suitable for use in hair care or other personal care compositions; wherein the ratio of Group I to Group II surfactants is from about 100:0 to about 30:70. In another embodiment of the present invention the ratio of Group I to Group II surfactants is from about 85:15 to about 40:60. In yet another embodiment of the present invention the ratio of Group I to Group II surfactants is from about 70:30 to about 55:45.

Non limiting examples of anionic surfactants are described in U.S. Pat. Nos. 2,486,921; 2,486,922; and 2,396,278. The anionic surfactant can be selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Additional suitable Group I and Group II surfactants include those disclosed in U.S. Patent Application No. 61/120,765 and those surfactants disclosed in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.). Other non-limiting examples of suitable surfactants are included in U.S. Ser. No. 61/120,790.

b. Non-Lathering Porous Dissolvable Solid Substrates

The non-lathering porous dissolvable solid substrates comprise from about 10% to about 75%, in another embodiment from about 15% to about 60%, and in another embodiment from about 20% to about 50% by weight of the personal care article of surfactant; wherein the surfactant comprises one or more of the surfactants described below.

(i) Anionic Surfactants

If the porous dissolvable solid substrate of the present invention is non-lathering, the substrate may comprise a maximum level of 10% (or less than 10%) of anionic surfactants to be used primarily as a process aid in making a stable foam solid. Additional, non-ionic surfactants can be combined with the anionic surfactants to reach a surfactant level which generates a stable foam solid prior to drying.

(ii) Cationic Surfactants

In one embodiment cationic surfactants are included as a process aid in making a stable porous dissolvable solid substrate. Suitable cationic surfactant actives for use in compositions of the invention contain amino or quaternary ammonium hydrophilic moieties which are positively charged when dissolved in the composition.

Suitable quaternary ammonium cationic surfactant useful herein include, but are not limited to, those having the formula (I):

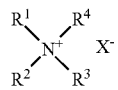

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate, nitrate, sulphate, and alkylsulphate radicals. In one embodiment, the alkyl sulphate radical is metho sulfate and/or etho sulfate.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated and can be branched or unbranched. In one embodiment, the class of cationic surfactants of general formula (I), $R^1$ and $R^2$ are each independently selected from $C_{16}$ to $C_{22}$ hydrocarbyl chains comprising at least one ester linkage in both $R^1$ and $R^2$, and $R^3$ and $R^4$ are each independently selected from $CH_3$ and $CH_2CH_2OH$. In another embodiment, the class of cationic surfactants of general formula (I), $R^1$ and $R^2$ are each independently selected from $C_{16}$ to $C_{22}$ saturated or unsaturated, and $R^3$ and $R^4$ are each independently selected from $CH_3$, $CH_2CH_2OH$, and $CH_3$. In yet another embodiment, the class of cationic surfactants of general formula (I), $R^1$ is a $C_{16}$ to $C_{22}$ alkyl chain and $R^2$, $R^3$ and $R^4$ are each independently selected from $CH_3$, $CH_2CH_2OH$, and $CH_3$.

Suitable quaternary ammonium cationic surfactants of general formula (I) can include cetyltrimethylammonium chloride, behenyltrimethylammonium chloride (BTAC), stearyltrimethylammonium chloride, cetylpyridinium chloride, octadecyltrimethylammonium chloride, hex adec yltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, distearyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

In a particular embodiment, the quaternary ammonium cationic surfactants for use in the invention are cetyltrimethylammonium chloride, available commercially, for example as GENAMIN CTAC by Clariant and Arquad 16/29 supplied by Akzo Nobel, behenyltrimethylammonium chloride (BTMAC) such as GENAMIN KDMP supplied by Clariant, and distearyldimethylammonium chloride such as GENAMIN DSAP supplied by Clariant. Mixtures of any of the foregoing materials may also be suitable. In a preferred embodiment, the quaternary ammonium cationic surfactant is behenyltrimethylammonium chloride (BTMAC).

Other suitable cationic surfactant conditioner actives can include salts of primary, secondary, and tertiary fatty amines. In one embodiment, the alkyl groups of such amines have from about 12 to about 22 carbon atoms, and can be substituted or unsubstituted. These amines are typically used in combination with an acid to provide the cationic species.

Suitable alkyl amine salts useful herein include, but are not limited to, those salts corresponding to alkyl amines having the general formula (II):

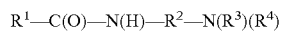

in which $R^1$ is a fatty acid chain containing from 12 to 22 carbon atoms, $R^2$ is an alkylene group containing from one to four carbon atoms, and $R^3$ and $R^4$ are, independently, an alkyl group having from one to four carbon atoms. $R^1$ can be saturated or unsaturated and can be branched or unbranched.

Suitable materials of general formula (II) are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Other suitable alkyl amine salts can include dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine. In a preferred embodiment, the alkyl amine salt is stearamidopropyldimethylamine. Mixtures of any of the foregoing materials may also be suitable.

The acid used to provide the cationic surfactant active can be any organic acid or mineral acid of sufficient acid strength to neutralize a free amine nitrogen. Such acids include hydrochloric acid, sulphuric acid, nitric acid, phosphoric acid, lactic acid, citric acid, tartaric acid, acetic acid, gluconic acid, glycolic acid and propionic acid, or combinations thereof. In one embodiment, a sufficient amount of acid is added to neutralize the amidoamine compound and to adjust the final pH of the composition to within a range of from about 2.5 to about 6; in another embodiment, from about 3 to about 5. In one embodiment, the molar ratio of protonatable amine groups to $H^+$ from the acid is from about 1:0.3 to about 1:1.2; and in another embodiment, from about 1:0.5 to about 1:1.1. Mixtures of any of the above-described cationic surfactants may also be suitable.

(iii) Non-Ionic Surfactants

In one embodiment non-ionic surfactants are included as a process aid in making a stable porous dissolvable solid substrate. Suitable nonionic surfactants for use in the present invention include those described in McCutcheon's Detergents and Emulsifiers, North American edition (1986), Allured Publishing Corp., and McCutcheon's Functional Materials, North American edition (1992). Suitable nonionic surfactants for use in the personal care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

(iv) Polymeric Surfactants

Polymeric surfactants can also be surfactants to be employed as a process aid in making the porous dissolvable solid substrate of the present invention, either alone or in combination with ionic and/or nonionic surfactants. Suitable polymeric surfactants for use in the personal care compositions of the present invention include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

2. Water-Soluble Polymer ("Polymer Structurant")

The porous dissolvable solid substrate comprises water-soluble polymers that function as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have solubility in water, measured at 25° C., of from about 0.1 gram/liter (g/L) to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The one or more water-soluble polymers may be present from about 10% to about 50% by weight of the porous dissolvable solid substrate, in one embodiment from about 15% to about 40% by weight of the porous dissolvable solid substrate, and in yet another embodiment from about 20% to about 30% by weight of the porous dissolvable solid substrate.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous dissolvable solid substrate.

In one embodiment, at least one of the one or more water-soluble polymers is chosen such that about 2% by weight solution of the water-soluble polymer gives a viscosity at 20° C. of from about 4 centipoise to about 80 centipoise; in an alternate embodiment from about 5 centipoise to about 70 centipoise; and in another embodiment from about 6 centipoise to about 60 centipoise.

The water-soluble polymer(s) of the present invention can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. The water-soluble polymer(s) which are suitable may also be selected from naturally sourced polymers including those of plant origin examples which are described in U.S. Ser. No. 61/120,786. Modified natural polymers are also useful as water-soluble polymer(s) in the present invention and are included in U.S. Ser. No. 61/120,786. In one embodiment, water-soluble polymers of the present invention include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, and carboxymethycelluloses. In another embodiment, water-soluble polymers of the present invention include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name.

In a particular embodiment, the above mentioned water-soluble polymer(s) may be blended with any single starch or combination of starches as a filler material in such an amount as to reduce the overall level of water-soluble polymers required, so long as it helps provide the personal care article with the requisite structure and physical/chemical characteristics as described herein.

In such instances, the combined weight percentage of the water-soluble polymer(s) and starch-based material generally ranges from about 10% to about 50%, in one embodiment from about 15% to about 40%, and in a particular embodiment from about 20% to about 30% by weight relative to the total weight of the porous dissolvable solid substrate. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof. The starch-based materials may also include native starches that are modified using any modification known in the art, including those described in U.S. Ser. No. 61/120,786.

3. Plasticizer

The porous dissolvable solid substrate of the present invention comprises a water soluble plasticizing agent suitable for use in personal care compositions. In one embodiment, the one or more plasticizers may be present from about 1% to about 30% by weight of the porous dissolvable solid substrate; in another embodiment from about 3% to about 25%; in another embodiment from about 5% to about 20%, and in yet another embodiment, from about 8% to about 15%. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Suitable examples of polycarboxylic acids for use herein are disclosed in U.S. Ser. No. 61/120,786.

In one embodiment, the plasticizers include glycerin or propylene glycol and combinations thereof. European Patent Number EP283165B1 discloses other suitable plasticizers, including glycerol derivatives such as propoxylated glycerol.

4. Optional Ingredients

The porous dissolvable solid substrate may further comprise other optional ingredients that are known for use or otherwise useful in personal care compositions, provided that such optional materials are compatible with the selected essential materials described herein, or do not otherwise unduly impair the performance of the personal care composition.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Examples of such optional ingredients are disclosed in U.S. Ser. Nos. 12/361,634, 10/392,422 filed Mar. 18, 2003; and US Publication 2003/0215522A1, dated Nov. 20, 2003.

Other optional ingredients include organic solvents, especially water miscible solvents and co-solvents useful as solubilizing agents for polymeric structurants and as drying accelerators. Examples of suitable organic solvents are disclosed in U.S. Ser. No. 12/361,634. Other optional ingredients include: latex or emulsion polymers, thickeners such as water soluble polymers, clays, silicas, ethylene glycol distearate, deposition aids, including coacervate forming components. Additional optional ingredients include anti-dandruff actives including but not limited to zinc pyrithione, selenium sulfide and those actives disclosed in US Publication 2003/0215522A1.

B. Surface Resident Coating Comprising a Water Sensitive Active

In one embodiment, the porous dissolvable solid substrates provide a continuous and accessible high surface area "scaffold" (a 3-D network of "struts") for the surface resident coating comprising a water sensitive active to be adsorbed or distributed across creating a high surface area thin coating. This location puts the coating in position to immediately contact water during use.

The surface resident coating of the present invention comprises one or more water sensitive actives, including, but not limited to, actives that on their own are chemically unstable within an aqueous environment or that are chemically unstable in combination with other actives within an aqueous environment.

In one embodiment the surface resident coating comprises from about 10% to about 100% of one or more water sensitive actives; in another embodiment from about 25% to about 100%, and in yet another embodiment from about 40% to about 100%. In one embodiment the ratio of the porous dissolvable solid substrate to the surface resident coating comprising the water sensitive active is from about 110:1 to about 0.1:1, in another embodiment from about 20:1 to about 0.2:1, and in another embodiment from about 10:1 to about 0.3:1, and in yet another embodiment from about 1:1 to about 0.4:1.

The water sensitive actives may also be selected from chemical adjuvants (pH buffers, chelants, antioxidants etc.) that can modify the reactivity of one or more other water sensitive actives to either improve the stability profile during the shelf life of the product (in the presence of potential residual moisture levels) or to attenuate or accentuate or otherwise improve the intended activity of the one or more water sensitive actives on the substrate (skin or hair) during consumer usage.

The water sensitive actives of the present invention include oxidative bleaching and dyeing compounds which include but are not limited to: developer dye compounds, coupler dye compounds, oxidizing agents, chelants, pH modifiers and buffering agents, carbonate ion sources, radical scavenger systems, peroxide stabilizing agents, effervescent agents, warming agents, and color indicator agents.

1. Oxidative Dye Compounds

The compositions of the present invention may include oxidative dye compounds in the form of primary intermediates or couplers. The compounds suitable for use in the inventive compositions (including those optionally added), in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

These compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are: 1,7-Dihydroxynaphthalene (1,7-NAPHTHALENEDIOL); 1,3-Diaminobenzene (m-PHENYLENEDIAMINE); 1-Methyl-2,5-diaminobenzene (TOLUENE-2,5-DIAMINE); 1,4-Diaminobenzene (p-PHENYLENEDIAMINE); 1,3-Dihydroxybenzene (RESORCINOL); 1,3-Dihydroxy-4-chlorobenzene, (4-CHLORORESORCINOL); 1-Hydroxy-2-aminobenzene, (o-AMINOPHENOL); 1-Hydroxy-3-aminobenzene (m-AMINOPHENOL); 1-Hydroxy-4-amino-benzene (p-AMINOPHENOL); 1-Hydroxynaphthalene (1-NAPHTHOL); 1,5-Dihydroxynaphthalene (1,5-NAPHTHALENEDIOL); 2,7-dihydroxynaphthalene (2,7-NAPHTHELENEDIOL); 1,4-Dihydroxybenzene (HYDROQUINONE); 1-Hydroxy-4-methylaminobenzene (p-METHYLAMINOPHENOL); 6-Hydroxybenzo-morpholine (HYDROXYBENZOMORPHOLINE); 1-Methyl-2-hydroxy-4-aminobenzene (4-AMINO-2-HYDROXY-TOLUENE); 1-Methyl-2-hydroxy-4-(2'-hydroxyethyl)aminobenzene (2-METHYL-5-HYDROXY-ETHYLAMINO-PHENOL); 1,2,4-Trihydroxybenzene (1,2,4-TRIHYDROXYBENZENE); 1-Phenol-3-methylpyrazol-5-on (PHENYLMETHYLPYRAZOLONE); 1-(2'-Hydroxyethyloxy)-2,4-diaminobenzene (2,4-DIAMINOPHENOXY-ETHANOL HCL); 1-Hydroxy-3-amino-2,4-dichlorobenzene (3-AMINO-2,4-DICHLORO-PHENOL); 1,3-Dihydroxy-2-methylbenzene (2-METHYLRESORCINOL); 1-Amino-4-bis-(2'-hydroxyethyl)aminobenzene (N,N-BIS(2-HYDROXY-ETHYL)-p-PHENYLENE-DIAMINE); 2,4,5,6-Tetraminopyrimidine (HC Red 16); 1-Hydroxy-3-methyl-4-aminobenzene (4-AMINO-m-CRESOL); 1-Hydroxy-2-amino-5-methylbenzene (6-AMINO-m-CRESOL); 1,3-Bis-(2,4-Diaminophenoxy)propane (1,3-BIS-(2,4-DIAMINO-PHENOXY)-PROPANE); 1-(2'-Hydroxyethyl)-2,5-diaminobenzene (HYDROXYETHYL-p-PHENYLENE DIAMINE SULPHATE); 1-Methoxy-2-amino-4-(2'-hydroxyethylamino)benzene, (2-AMINO-4-HYDROXYETHYLAMINOANISOLE); 1-Hydroxy-2-methyl-5-amino-6-chlorobenzene (5-AMINO-6-CHLORO-o-CRESOL); 1-Hydroxy-2-amino-6-methylbenzene (6-AMINO-o-CRESOL); 1-(2'-Hydroxyethyl)-amino-3,4-methylenedioxybenzene (HYDROXYETHYL-3,4-METHYLENE-DIOXY-ANILINE HCl); 2,6-Dihydroxy-3,4-dimethylpyridine (2,6-DIHYDROXY-3,4-DIMETHYLPYRIDINE); 3,5-Diamino-2,6-dimethoxypyridine (2,6-DIMETHOXY-3,5-PYRIDINEDIAMINE); 5,6-Dihydroxyindole (5,6-DIHYDROXY-INDOLE); 4-Amino-2-aminomethylphenol (2-AMINOETHYL-p-AMINO-PHENOL HCl); 2,4-Diamino-5-methylphenetol (2,4-DIAMINO-5-METHYL-PHENETOLE HCl); 2,4-Diamino-5-(2'-hydroxyethyloxy) toluene (2,4-DIAMINO-5-METHYLPHENOXYETHANOL HCl); 5-Amino-4-chloro-2-methylphenol (5-AMINO-4-CHLORO-o-CRESOL); 1,3-Bis(N(2-Hydroxyethyl)N(4-amino-phenyl)amino)-2-propanol (HYDROXYPROPYL-BIS-(N-HYDROXYETHYL-p-PHENYLENEDIAMINE)HCL); 6-Hydrorxyindole (6-HYDROXY-INDOLE); 2,3-Indolinedione (ISATIN); 3-Amino-2-methylamino-6-methoxypyridine (HC BLUE NO. 7); 1-Phenyl-3-methyl-5-pyrazolone (2,4-DIHYDRO-5-METHYL-2-PHENYL-3H-PYRAZOL-3-ONE); 2-Amino-3-hydroxypyridine (2-AMINO-3-HYDROXYPYRIDINE); 5-Amino-salicylic acid; 1-Methyl-2,6-bis(2-hydroxy-ethylamino)benzene (2,6-HYDROXYETHYLAMINO-TOLUENE); 4-Hydroxy-2,5,6-triaminopyrimidine (2,5,6-TRIAMINO-4-PYRIMIDINOL SULPHATE); 2,2'-[1,2-Ethanediyl-bis-(oxy-2,1-ethanediyloxy)]-bis-benzene-1,4-diamine (PEG-3,2',2'-DI-p-PHENYLENEDIAMINE); 5,6-Dihydroxyindoline (DIHYDROXYINDOLINE); N,N-Dimethyl-3-ureidoaniline (m-DIMETHYL-AMINO-PHENYLUREA); 2,4-Diamino-5-fluortoluenesulfatehydrate (4-FLUORO-6-METHYL-m-PHENYLENEDIAMINE SULPHATE); 1-Acetoxy-2-methylnaphthalene (1-HYDROXYETHYL-4,5-DIAMINOPYRAZOLE SULPHATE); 1-acetoxy-2-methylnaphthalene (2-METHYL-1-NAPHTHOL); 2-amino-5-ethylphenol (2-AMINO-5-ETHYLPHENOL); 2,4-dichloro-3-aminophenol (3-AMINO-2,4-DICHLOROPHENOL); and p-Anilinoaniline (N-PHENYL-P-PHENYLENEDIAMINE).

These can be used in the molecular form or in the form of peroxide-compatible salts.

2. Oxidizing Agent

The inventive compositions may comprise an oxidizing agent, present in an amount sufficient to bleach melanin pigment in hair and/or cause formation of dye chromophores from oxidative dye precursors (including developers and/or couplers when present). Inorganic peroxygen materials capable of yielding hydrogen peroxide in an aqueous medium are preferred and include but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, preferably sodium salts thereof), which may be incorporated as monohydrates, tetrahydrates, etc.; alkali metal bromates; enzymes; and mixtures thereof. In one embodiment, the oxidizing agents of the present invention are selected from percarbonates (such as sodium percarbonate, ammonium percarbonate and potassium percarbonate); and persulphates (such as sodium persulphate, ammonium persulphate, and potassium persulphate). In another embodiment, the oxidizing agents of the present invention are selected from sodium percarbonate and ammonium persulfate.

3. pH Modifiers and Buffering Agents

The inventive compositions may comprise a pH modifier and/or buffering agent in an amount that is sufficiently effective to adjust the pH of the composition to fall within a range from about 3 to about 13, in some embodiments from about 8 to about 12, and even from about 8 to about 11. In some embodiments, the pH range for the carbonate ion source as described herein below is from 8.5 to 9.5, preferably from 8 to 9. Suitable pH modifiers and/or buffering agents for use herein include, but are not limited to: ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

4. Carbonate Ion Source

The compositions of the present invention may further comprise in an embodiment at least one source of peroxymonocarbonate ions, preferably formed in situ from a source of hydrogen peroxide and a carbonate ion source. According to the present invention the compositions thus also may comprise at least a source of carbonate ions or carbamate ions or hydrocarbonate ions or any mixture thereof. Any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Suitable sources of carbonate ions, carbamate and hydrocarbonate ions include sodium hydrogen carbonate, potassium hydrogen carbonate, ammonium carbamate and mixtures thereof.

5. Radical Scavenger System

The inventive compositions may comprise a radical scavenger, in a sufficient amount to reduce damage to the hair during an oxidative bleaching or coloring process. The radical scavenger is preferably selected such that it is not an identical species as the alkalizing agent. The radical scavenger is a species that can react with a carbonate radical to convert the carbonate radical by a series of fast reactions to a less reactive species. Preferred radical scavengers may be selected from the classes of alkanolamines, amino sugars, amino acids and mixtures thereof, and may include, but are not limited to: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other preferred radical scavenger compounds include benzylamine, glutamic acid, imidazole, di-tert-butylhydroxytoluene, hydroquinone, catechol and mixtures thereof.

6. Chelants

The inventive compositions may comprise chelants in an amount sufficient to reduce the amount of metals available to interact with formulation components, particularly oxidizing agents, more particularly peroxides. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

7. Effervescent Actives

The effervescent of the present invention comprises a composition that is capable of effervescence. The term "effervescent," as defined herein, means any product capable of forming bubbles in liquid environments and may also be considered any product capable of liberating carbon dioxide in or out of liquid environments. Likewise, "effervescence" means forming bubbles in liquid environments or liberating carbon dioxide in or out of liquid environments.

In certain embodiments, the presence of bubbles results from the formation of carbon dioxide. For instance, when added to a liquid, such as water, a mixture of at least one acid and at least one salt results in a chemical reaction that liberates carbon dioxide. In one aspect, both the acid and the salt may be in anhydrous form.

Examples of acids suitable for use in these illustrative embodiments include, but are not limited to, tartaric acid, citric acid, fumaric acid, adipic acid, malic acid, oxalic acid, or sulfamic acid, either alone or in combination. Typically, the effervescent of these embodiments is prepared from citric acid or a combination of citric acid and tartaric acid.

Examples of salts suitable for use in illustrative embodiments include, but are not limited to, the alkali metal salts. Sodium carbonate, calcium carbonate, magnesium carbonate, ammonium carbonate, potassium carbonate, sodium bicarbonate, and calcium bicarbonate may all be employed.

In other embodiments, the selection of specific acids and/or salts and their proportions depends, at least in part, upon the requirements for the amount of carbon dioxide release. In some embodiments, the acid may be added in an amount of about 10% to about 60% by weight of the effervescent, while the alkali metal salt may also be added in an amount of about 10% to 60% by weight of the effervescent.

8. Warming Actives

Warming actives include heat generating agents, or heat generating powders which release heat via exothermic reactions (heat producing) when they are mixed with water during application. The heat generating agents of the present invention include, but are not limited to, inorganic salts, glycols, finely divided solid adsorbent materials, and iron redox systems. In one embodiment the warming actives are selected from the group consisting of anhydrous inorganic salts including, but not limited to calcium chloride, magnesium chloride, calcium oxide, magnesium sulphate, aluminium sulphate and combinations thereof. In yet another embodiment the warming actives of the present invention are selected from the group consisting of anhydrous calcium chloride, anhydrous magnesium chloride, anhydrous magnesium sulphate, and combinations thereof.

9. Color Indicators

The surface resident coatings of the present invention may also comprise color indicators. Such color indicators can be present in an amount sufficient to result in a visual color change when the indicator is contacted with water. The term "visual color change" refers to a color change that can be detected by the human eye, either alone, or with the aid of an energy source such as a black light. The color indicators of the present invention can include, but are not limited to, those selected from the group consisting of pH indicators, photoactive pigments, thermochromatic pigments, and combinations thereof. In one embodiment the color changes from red to blue, in another embodiment from red to yellow, and in another embodiment from yellow to green, and in yet another embodiment from blue to red, and in yet another embodiment from colorless to color, and in yet another embodiment from color to colorless.

In one embodiment the color change is a pH sensitive color changing component. The color indicators can be selected from the group consisting of bromocresol green, phenolphthalein, o-cresolphthalein, thymolphthalein, coumarin, 2,3-dioxyxanthone, coumeric acid, 6,8-dinitro-2,4(1H) quinazolinedione, ethyl-bis(2,4-dimethylphenyl)ethanoate, and combinations thereof.

10. Optional Ingredients:

Optional ingredients may also be included in the surface resident coatings of the present invention. Optional ingredients include non oxidative hair dyes i.e. direct dyes which may be used alone or in combination with the above described oxidative dyes. Suitable direct dyes include azo or anthraquinone dyes and nitro derivatives of the benzene series and or melanin precursors and mixtures thereof. Such direct dyes are particularly useful to deliver shade modification or highlights. Particularly embodiments are Basic Red 51, Basic Orange 31, Basic Yellow 87 and mixtures thereof.

The surface resident coatings of the present invention may also include a non-hygroscopic solvent to mitigate moisture from the environment precipitating a premature reaction with or between the water sensitive active or actives, before these chemical constituents come into contact with liquids. The term non-hygroscopic solvent is defined herein as any compound that does not take up moisture from the environment. In some embodiments, the non-hygroscopic solvent is capable of dissolving or dispersing at least a small amount of one or more other substances. Such non-hygroscopic solvents include, but are not limited to diethyl phthalate, isopropyl myristate, isopropyl palmitate and at least some species of ester solvents, such as dioctyl adipate and butyl stearate. In other embodiments, the non-hygroscopic solvent may be non-polar (aprotic).

The surface resident coatings of the present invention may encompass water sensitive actives in particulate form that are at least partially coated with anhydrous oils and/or waxes. Examples of waxes include, but are not limited, to natural waxes and derivatives of such waxes (derived from plants and animals) and synthetic waxes.

The surface resident coatings of the present invention may also include water absorbents such as Vermiculite as an inexpensive water reservoir. Vermiculite is an aluminum-iron magnesium silicate. In certain systems salts such as sodium chloride may be employed to further assist the reaction. Cosmetic product dispensers are preferred which seal the product from the atmosphere during storage periods.

The surface resident coating of the present invention is applied to the porous dissolvable solid substrate. In one embodiment, the surface resident coating is in the form of a fine powder. As seen in FIG. 1, in certain embodiments of the present invention, the personal care article 10 contains a surface resident coating 12 that is located on at least a portion of the surface of the porous dissolvable solid substrate 14. It will be appreciated that the surface resident coating 12 may not always be adjacent to the porous dissolvable solid substrate 14. In certain embodiments, the surface resident coating 12 may permeate the porous dissolvable solid substrate 14 in whole or in part.

Figure 3A:
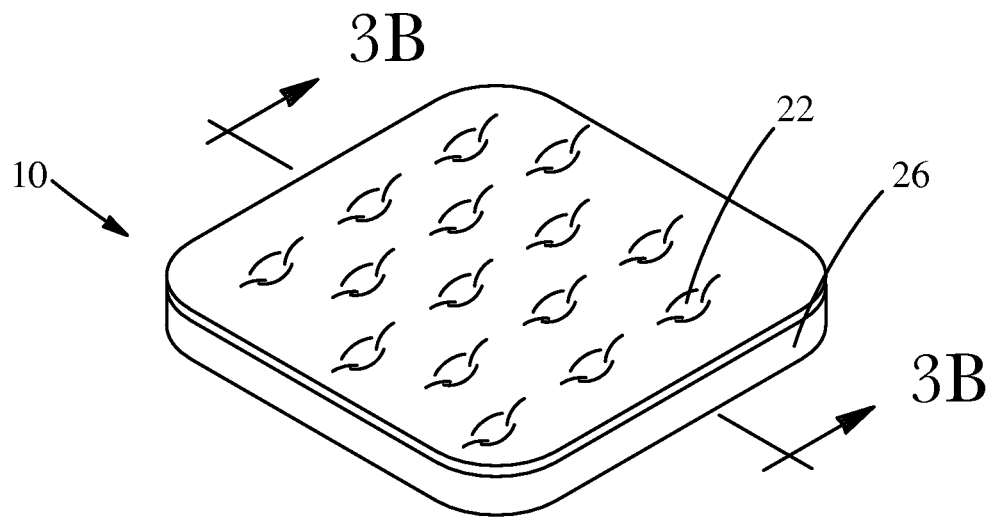
FIG. 3 is a schematic view of a dimpled porous dissolvable solid substrate with a surface resident coating comprising a water sensitive active inside the dimples.
Figure 3B:
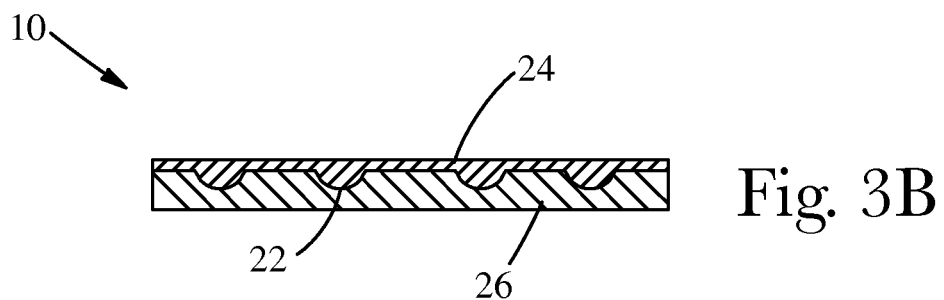

Alternatively, the surface resident coating can be included (e.g., sandwiched or encased) within the personal care article or parts thereof. Such a surface resident coating can be sprayed, dusted, sprinkled, coated, surface-printed (e.g., in the shape of a desired adornment, decoration, or pattern), poured on, injected into the interior, dipped, or by any other suitable means, such as by use of a depositor, sifter, or powder bed. In the embodiments depicted by FIGS. 3A, 3B, and 4, the personal care article 10 contains a surface resident coating that can be situated below the surface of the porous dissolvable solid substrate. As seen in FIG. 3B which is a cross sectional view of the personal care article 10, the surface resident coating 24 is located within the dimples 22 of the porous dissolvable solid substrate 26.

Figure 2:
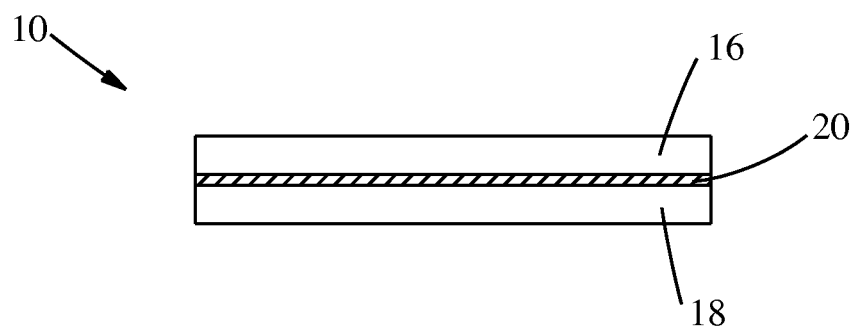
FIG. 2 is a schematic view of two porous dissolvable solid substrates with a surface resident coating comprising a water sensitive active.

Referring now to FIG. 2, in certain embodiments the powder is sandwiched between two porous dissolvable solid substrate which are then joined together (e.g., via sealing the adjoining surfaces or edges with a thin layer of water and/or plasticizer so as to not substantially dissolve the porous dissolvable solid substrate and applied pressure to induce adhesion). In this embodiment, the personal care article 10 comprises two porous dissolvable solid substrates 16, 18 in between which a surface resident coating 20 is located.

Figure 4:
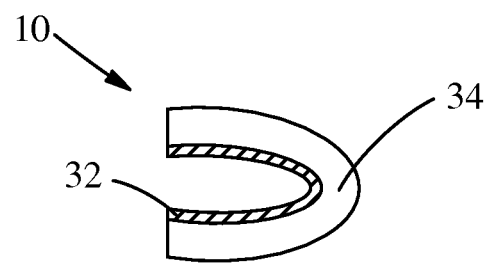
FIG. 4 is a schematic view of a porous dissolvable solid substrate that is folded over to enclose a surface resident coating comprising a water sensitive active.

Alternatively, in certain embodiments, the powder may be on one personal care article which is folded over to form a pouch, encasing the powder. As depicted in FIG. 4, the personal care article 10 comprises a surface resident coating 32 that is enclosed within a folded porous dissolvable solid substrate 34.

The personal care article may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the personal care article, for example the personal care article can be formed originally in a dimpled or waffle pattern. The raised portions can also be the result of creping processes, imprinted coatings, embossing patterns, laminating to other layers having raised portions, or the result of the physical form of the porous dissolvable solid substrate itself. The texturing can also be the result of laminating one porous dissolvable solid substrate to a second porous dissolvable solid substrate that is textured. In a particular embodiment, the personal care article can be perforated with holes or channels penetrating into or through the porous solid.

III. Product Form of the Personal Care Article

The personal care article can be produced in any of a variety of product forms, including porous dissolvable solid substrates along with the surface resident coating comprising the water sensitive actives used alone or in combination with other personal care components. Regardless of the product form, the product form embodiments contemplated herein include the selected and defined personal care article that comprises a combination of a porous dissolvable solid substrate and a surface resident coating comprising a water sensitive active.

In one embodiment, the personal care article is in the form of one or more flat sheets or pads of an adequate size to be able to be handled easily by the user. It may have a square, rectangle or disc shape or any other suitable shape. The pads can also be in the form of a continuous strip including delivered on a tape-like roll dispenser with individual portions dispensed via perforations and or a cutting mechanism. Alternatively, the personal care articles are in the form of one or more cylindrical objects, spherical objects, tubular objects or any other shaped object.

The personal care article may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the personal care article, for example the personal care article can be formed originally in a dimpled or waffle pattern. The raised portions can also be the result of creping processes, imprinted coatings, embossing patterns, laminating to other layers having raised portions, or the result of the physical form of the porous dissolvable solid substrate itself. The texturing can also be the result of laminating one porous dissolvable solid substrate to a second porous dissolvable solid substrate that is textured. In a particular embodiment, the personal care article can be perforated with holes or channels penetrating into or through the porous solid.

IV. Method of Manufacture

The personal care article can be prepared by the process comprising: (1) Preparing a processing mixture comprising surfactant(s), dissolved polymer structurant, and plasticizer; (2) Aerating the processing mixture by introducing a gas into the processing mixture to form an aerated wet mixture; (3) Forming the aerated wet mixture into one or more desired shapes; (4) Drying the aerated wet mixture to form a porous dissolvable solid substrate; and (5) Applying the surface resident coating comprising a water sensitive active in powdered form to the porous dissolvable solid substrate.

A. Preparation of Processing Mixture

The processing mixture is generally prepared by dissolving the polymer structurant in the presence of water, plasticizer, surfactant and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including stepwise processing via pre-mix portions of any combination of ingredients.

The processing mixtures of the present invention comprise: from about 15% to about 60% solids, in one embodiment from about 20% to about 55% solids, in another embodiment from about 25% to about 50% solids, and in yet another embodiment from about 30% to about 45% solids by weight of the processing mixture before drying; and have a viscosity of from about 2,500 cps to about 150,000 cps, in one embodiment from about 5,000 cps to about 100,000 cps, in another embodiment from about 7,500 cps to about 75,000 cps, and in still another embodiment from about 10,000 cps to about 60,000 cps.

The % solids content is the summation of the weight percentages by weight of the total processing mixture of all of the solid, semi-solid and liquid components excluding water and any obviously volatile materials such as low boiling alcohols. The processing mixture viscosity values are measured using a TA Instruments AR500 Rheometer with 4.0 cm diameter parallel plate and 1,200 micron gap at a shear rate of 1.0 reciprocal seconds for a period of 30 seconds at 23° C.

B. Aeration of Processing Mixture

The aeration of the processing mixture is accomplished by introducing a gas into the mixture. In one embodiment this is done by mechanical mixing energy. In another embodiment this may be achieved via chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In a particular embodiment, it has been discovered that the personal care article can be prepared within continuous pressurized aerators that are conventionally utilized within the foods industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

Aeration can also be accomplished with chemical foaming agents by in-situ gas formation (via chemical reaction of one or more ingredients, including formation of carbon dioxide ($CO_2$ (g)) by an effervescent system. An additional possibility is aeration via volatile blowing agents such as low boiling hydrocarbons or alcohols including, but not limited to, isopentane, pentane, isobutene, ethanol etc.

In one embodiment, the pre-mixture is pre-heated immediately prior to the aeration process at above ambient temperature but below any temperatures that would cause undesirable degradation of any of the components. In one embodiment, the pre-mixture is kept at above about 40° C. and below about 99° C., in another embodiment above about 50° C. and below about 95° C., in another embodiment above about 60° C. and below about 90° C. In one embodiment, when the viscosity at ambient temperature of the pre-mix is from about 20,000 cps to about 150,000 cps, the optional continuous heating should be utilized before the aeration step. In another embodiment, additional heat is applied during the aeration process to try and maintain an elevated temperature during the aeration. This can be accomplished via conductive heating from one or more surfaces, injection of steam, a surrounding hot water bath, or other processing means.

In one embodiment the wet density range of the aerated pre-mixture ranges from about 0.12 $g/cm^3$ to about 0.50 $g/cm^3$, in another embodiment from about 0.15 $g/cm^3$ to about 0.45 $g/cm^3$, in another embodiment from about 0.20 $g/cm^3$ to about 0.40 $g/cm^3$, and in yet another embodiment from about 0.25 $g/cm^3$ to about 0.35 $g/cm^3$.

C. Forming the Aerated Wet Processing Mixture

The forming of the aerated wet processing mixture may be accomplished by any suitable means to form the mixture in a desired shape or shapes including, but not limited to (i) depositing the aerated mixture to moulds of the desired shape and size comprising a non-interacting and non-stick surface including aluminium, Teflon, metal, HDPE, polycarbonate, neoprene, rubber, LDPE, glass and the like; (ii) depositing the aerated mixture into cavities imprinted in dry granular starch contained in a shallow tray, otherwise known as starch moulding forming technique; and (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

D. Drying the Aerated Wet Processing Mixture into a Porous Dissolvable Solid Substrate The drying of the formed aerated wet processing mixture may be accomplished by any suitable means including, but not limited to (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, and (x) conveyor driers, and combinations thereof. Any suitable drying means that does not comprise freeze-drying can be used.

The drying temperature may range from about 40° C. to about 200° C. In a one embodiment, the drying environment is heated to a temperature between 100° C. and 150° C. In one embodiment, the drying temperature is between 105° C. and 145° C. In another embodiment, the drying temperature is between 110° C. and 140° C. In a further embodiment, the drying temperature is between 115° C. and 135° C.

Other suitable drying environments include "volumetric heating" techniques using high frequency electromagnetic fields such as Microwave Drying and Radio Frequency (RF) Drying. With these techniques, the energy is transferred electromagnetically through the aerated wet pre-mixture rather than by conduction or convection.

Optional ingredients may be imparted during any of the above described four processing steps or even after the drying process.

E. Preparing the Surface Resident Coating Comprising the Water sensitive active

The preparation of the surface resident coating comprising the water sensitive active may include any suitable mechanical, chemical, or otherwise means to produce a particulate composition comprising the water sensitive active including any optional materials as described herein.

Particle size is known to have a direct effect on the potential reactive surface area of the water sensitive actives and thereby has a substantial effect on how fast the water sensitive active delivers the intended beneficial effect upon dilution with water. In this sense, the water sensitive actives with smaller particle sizes tend to give a faster and shorter lived effect, whereas the water sensitive actives with larger particle sizes tend to give a slower and longer lived effect. In one embodiment the surface resident coatings of the present invention may have a particle size from about 1 μm to about 200 μm, in another embodiment from about 2 μm to about 100 μm, and in yet another embodiment from about 3 μm to about 50 μm.

In some embodiments, it is helpful to include inert fillers within the grinding process, for instance aluminum starch octenylsuccinate under the trade name DRY-FLO® PC and available from Akzo Nobel, at a level sufficient to improve the flow properties of the powder and to mitigate inter-particle sticking or agglomeration during powder production or handling. Other optional excipients or cosmetic actives, as described herein, can be incorporated during or after the powder preparation process, e.g., grinding, milling etc. The resulting powder may also be blended with other inert powders, either of inert materials or other powder-active complexes, and including water absorbing powders as described herein.

In one embodiment, the water sensitive actives may be surface coated with non-hygroscopic solvents, anhydrous oils, and/or waxes as defined herein. This may include the steps of: (i) coating the water sensitive powder with the non-hydroscopic solvents, anhydrous oils, and/or waxes; (ii) reduction of the particle size of the water sensitive active particulates, prior to, during, or after a coating is applied, by known mechanical means to a predetermined size or selected distribution of sizes; and (iii) blending the resulting coated particulates with other optional ingredients in particulate form. Alternatively, the coating of the non-hydroscopic solvents, anhydrous oils and/or waxes may be simultaneously applied to the other optional ingredients, in addition to the water sensitive actives, of the surface resident coating composition and with subsequent particle size reduction as per the procedure described above.

F. Combining Surface Resident Coating comprising the Water Sensitive Actives with the Porous Dissolvable Solid Substrate Any suitable application method can be used to apply the surface resident coating comprising water sensitive active to the personal care article such that it forms a part of the personal care article. For instance, the porous dissolvable solid substrate can have a tacky surface by drying the porous dissolvable solid substrate's surface to a specific water content before application of powder to facilitate the adherence of the surface resident coating comprising the water sensitive actives to the porous solid. In one embodiment, the porous dissolvable solid substrate is dried to a moisture content of from about 0.1% to about 25%, in one embodiment from about 3% to about 25%, in another embodiment from about 5% to about 20% and in yet another embodiment from about 7% to about 15%. Alternatively, a previously dried dissolvable porous solid substrate's surface can be made to reversibly absorb a desired level of atmospheric moisture prior to application of the powder within a controlled humidity environment for a specific period of time until equilibrium is achieved. In one embodiment, the humidity environment is controlled from about 20% to about 85% relative humidity; in another embodiment, from about 30% to about 75% relative humidity; and in yet another embodiment, from about 40% to about 60% relative humidity.

In another embodiment, the porous dissolvable solid substrate is placed in a bag, tray, belt, or drum containing or otherwise exposed to the powder and agitated, rolled, brushed, vibrated or shaken to apply and distribute the powder, either in a batch or continuous production manner. Other powder application methods may include powder sifters, electrostatic coating, tribo charging, fluidized beds, powder coating guns, corona guns, tumblers, electrostatic fluidized beds, electrostatic magnetic brushes, and/or powder spray booths. The surface resident coating comprising the water sensitive active can be applied over portions or entire regions of the porous dissolvable solid substrate's exterior surface, and can be applied in a manner to adorn, decorate, form a logo, design, etc.

V. Test Methods

A. Dissolution Rate

The personal care article of present invention has a Dissolution Rate that allows the personal care article to rapidly disintegrate during use application with water. The Dissolution Rate of the personal care article is determined in accordance with the methodology described below.

Hand Dissolution Method: 0.5 to 1.5 g (approximately 10 to 20 square centimeters if in a 3 to 10 mm thick sheet/pad form) of the personal care article (as described in the examples herein) is placed in the palm of the hand while wearing nitrile gloves. 7.5 $cm^3$ of warm tap water (from about 30° C. to about 35° C.) is quickly applied to the personal care composition via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum. For the latter scenario, the weight of the undissolved material is also reported.

The personal care articles of the present invention have a hand dissolution value of from about 1 to about 30 strokes, in one embodiment from about 2 to about 25 strokes, in another embodiment from about 3 to about 20 strokes, and in still another embodiment from about 4 to about 15 strokes.

B. Thickness

The thickness of the personal care article and/or the porous dissolvable solid substrate is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 phi (6.32 gm/cm$^2$).

The thickness of the personal care article and/or the porous dissolvable solid substrate is measured by raising the platen, placing a section of the sample on the stand beneath the platen, carefully lowering the platen to contact the sample, releasing the platen, and measuring the thickness of the sample in millimeters on the digital readout. The sample should be fully extended to all edges of the platen to make sure thickness is measured at the lowest possible surface pressure, except for the case of more rigid samples which are not flat. For more rigid samples which are not completely flat, a flat edge of the sample is measured using only one portion of the platen impinging on the flat portion of the sample. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

C. Basis Weight

The Basis Weight of the personal care article and/or the porous dissolvable solid substrate is calculated as the weight of the personal care article and/or the porous dissolvable solid substrate per area of the selected personal care article and/or the porous dissolvable solid substrate (grams/m$^2$). The area is calculated as the projected area onto a flat surface perpendicular to the outer edges of the personal care article and/or the porous dissolvable solid substrate. For a flat object, the area is thus computed based on the area enclosed within the outer perimeter of the sample. For a spherical object, the area is thus computed based on the average diameter as 3.14× (diameter/2)$^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side.

D. Solid Density

The porous dissolvable solid substrate of the personal care compositions described herein can be characterized in terms of a solid density determination.

The solid density of the porous dissolvable solid substrate can be determined by dividing the weight of the solid by the known volume of the solid. The latter can be determined by a number of techniques including producing the solid within a mold of known x-y dimensions and measuring the resulting thickness to account for any shrinkage or expansion during the drying process. The solid can also be cut to known x-y dimensions, i.e., by using a circular or square cutting die of known diameter or dimensions and then by measuring the thickness. Alternatively, in the instances where there are not any significant thickness variations, the density can be calculated by the equation: Calculated Density=Basis Weight of porous solid/(Average porous Solid Thickness×1,000).

E. Cell Inter-Connectivity

The personal care article and/or the porous dissolvable solid substrate of the present invention have a high degree of cell inter-connectivity, i.e., are predominantly open-celled solid foams as opposed to being predominantly closed-cell solid foams. The cell inter-connectivity can be assessed by light microscopy, scanning electron microscopy, micro computed tomography imaging parameters (Star Volume and SMI Index), gas pycnometry parameters (% Open Cells), or other suitable methodology.

A qualitative method of determining cell inter-connectivity is via light microscopy. This is performed by cutting a 2-3 mm wide sliver of the personal care article and/or the porous dissolvable solid substrate in the z-direction using scissors or a sharp blade, measured across the normal x-y largest surface, and turning the resulting sliver by 90 degrees to reveal the internal cellular structure of the freshly cut cross-sectional area. This cross-sectional area can be assessed by close visual inspection or, more accurately, by employing magnification under a stereo microscope such as the SZX12 Stereo microscope available from Olympus America Inc., Center Valley, Pa. The open-celled personal care article and/or the porous dissolvable solid substrate of the present invention can easily be identified by examining the inner portion of the cross-sectional area which comprises a predominantly three dimensional network of struts with open void spaces surrounding the struts that are inter-connected to one another including in the third dimension through the depth of the cross-section. In contrast, the inner cross-section of a closed-cell foam appears as discrete bubbles that are cut across and then only being inter-connected at the cross-sectional surface in two dimensions by virtue of the cutting process employed to generate the exposed cross-sectional area.

Another means to determine the cell interconnectivity is via the Star Volume and the Structure Model Index. Disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 - \frac{BV - \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, StarVolume measurements are made. Star Volume is a measure of the "openness" of the void space in a two phase structure. By choosing a random uniformly distributed set of points in the phase of interest (in our case this is the background), we can extend lines in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (we only want to accept lines that actually intersect with the foreground phase). The final equation is based upon the research published in *Star volume in bone research. A histomorphometric analysis of trabecular bone structure using vertical sections*; Vesterby, A.; Anat Rec.; 1993 February; 235(2):325-334.:

$$StarVolume = \frac{4}{3}\pi - \frac{\sum dist^3}{N}$$

where "dist" is the individual distances and N is the number of lines examined.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

ASTM Standard Test Method D2856 provides a procedure for determining the percentage of open cells using an older model of an air comparison pycnometer. This device is no longer manufactured. However, you can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde On and Paul Webb.

F. Cell Wall Thickness

The Cell Wall Thickness of the personal care article and/or the porous dissolvable solid substrate is computed from the scanned images via a micro computed tomography system (μCT80, SN 06071200, Scanco Medical AG) as described herein. The Cell Wall Thickness is determined according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

G. Specific Surface Area

The Specific Surface Area of the personal care article and/or the porous dissolvable solid substrate is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the degassed sample+sample tube weight. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved.

Sample Preparation (Degassing): A sample not adequately cleaned of adsorbed contaminants will outgas during an analysis and some portion of the surface will be inaccessible to measurement. The purpose of degassing is to remove these adsorbed molecules from the surface of the sample prior to analysis. Adsorptive molecules must reach all parts of the surface for the true surface area to be revealed. Samples are prepared by heating the sample while simultaneously evacuating the sample tube.

For these experiments, the samples are outgassed under evacuation at room temperature overnight. Samples may then analyzed using an ASAP 2420 with krypton gas adsorption. Krypton gas is preferred over nitrogen gas as it has a saturation pressure approximately 1/300 that of nitrogen at liquid nitrogen temperature (krypton: 2.5 torr; nitrogen: 760 torr). Therefore, compared to nitrogen, there is in the free space above the sample about 1/300 the number of krypton molecules present at the same relative pressure. Since about the same number of krypton and nitrogen molecules are required to form a monolayer, this number represents a far greater proportion of the quantity dosed than in the case of nitrogen. These measurements can be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

H. Evaluation of Surface Resident Coating

The presence of a surface resident coating comprising a water sensitive active of the present invention can be determined by a number of techniques. For detection of a particulate or powder coating, the surface of application as well as the cross-sections perpendicular to the larger surfaces of the porous dissolvable solid substrate can be examined by microscopic techniques. These microscopic techniques may include light microscopy and scanning electron microscopy (SEM). The light microscopy may include but are not necessarily limited to bright field, dark field, or confocal microscopy techniques. Other techniques for mapping unique elements such as silicon or distinctive functional groups such as quaternary ammonium groups on the cross-sectional surface include: time of flight secondary ion mass spectroscopy (ToF-SIMS), or infrared microscopy.

Potential methods for looking at the distribution of particles from the surface to the interior of the porous dissolvable solid substrate without sectioning the samples include: micro-Computed Tomography (micro-CT), Magnetic Resonance Imaging (MRI), Acoustic Imaging, Confocal Fluorescence Microscopy, Confocal Raman Spectroscopy, and Confocal Infrared Reflectance Spectroscopy.

The determination of surface-resident coating particles on cross-sectioned porous dissolvable solid substrate can be performed by comparing the distribution of the particles across the cut cross-section of the porous solid. Specifically, the surface resident coating particles should be present at the original solid/air interfaces, but not within the exposed cross sectioned interior of the solid cell walls as can be ascertained by analyzing the exposed freshly cut cross-sectional interiors of the solid. It should be noted that some contamination of the freshly cut cross-sectional solid cell wall interiors may occur as a consequence of the cutting process of the porous solid. However, the preponderance (in one embodiment, from about 50% to about 100%) of the surface resident coating particle distribution will occur at the original solid/air interfaces and not within the exposed cut cross-sectional interiors of the cell walls.

It should also be noted that the surface resident coating particles of the present invention generally do not spread uniformly across all exposed solid/air interfaces. Rather, it has been found that the surface resident coatings of the present invention typically spread, from the point of coating application, into cavities down to about 0.5 to about 3.0 mm according to gravity. Accordingly, the determination of surface resident particles of cosmetic actives of the present invention (as described above), should be conducted across many different cross sections from top-to-bottom and from edge-to-edge of the porous solid. If present, the surface resident cosmetic active particle will generally be within the regional vicinity (to within about 0.5 to about 3.0 mm from the surface) of the surface to where the coating was first applied.

IV. Methods of Use

The compositions of the present invention may be used for treating mammalian keratinous tissue such as hair and/or scalp, and provide rapid rinse-ability. The method for conditioning the hair may comprise the steps of: a) applying an effective amount of the personal care product to the hand, b) wetting the personal care product with water and rubbing to dissolve the solid, c) applying the dissolved material to either the hair or scalp such as to treat, and d) rinsing the diluted treatment from the hair or scalp using water. These steps can be repeated as many times as desired to achieve the desired treatment benefit.

V. Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

Preparation of Porous Dissolvable Solid Substrate Shampoo

The following porous dissolvable substrate is prepared in accordance to the present invention from the following processing mixture:

TABLE 1

| Component | Wt % |
|---|---|
| Distilled water | 23.4 |
| Glycerin | 2.9 |
| Polyvinyl alcohol[1] | 7.3 |
| Ammonium Laureth-3 sulfate (25% activity) | 40.0 |
| Ammonium Lauryl sulfate (25% activity) | 24.0 |
| Cetyl alcohol | 0.9 |
| Cocamide MEA | 1.5 |
| Total | 100.0 |

[1]CELVOL ® 523 available from Celanese Corporation (Dallas, Texas)

Into an appropriately sized and cleaned vessel, the distilled water and glycerin is added with stirring at 100-300 rpm. The CELVOL® 523 is weighed into a suitable container and slowly added to the main mixture in small increments using a spatula while continuing to stir while avoiding the formation of visible lumps. The mixing speed is adjusted to minimize foam formation. The mixture is slowly heated to 75° C. after which the ammonium laureth-3 sulfate and ammonium lauryl sulfate are added. The mixture is allowed to again reach 75° C. and the cetyl alcohol and cocamide MEA is added. The mixture is then heated to 85° C. while continuing to stir and then allowed to cool to room temperature. The final pH is between 5.2-6.6 and adjusted with citric acid or diluted sodium hydroxide if necessary. The viscosity of the mixture is approximately 12,000 to 15,000 cps at 1 s$^{-1}$.

250 grams of the above mixture is transferred into a 5 quart stainless steel bowl of a KITCHENAID® Mixer Model K5SS (available from Hobart Corporation, Troy, Ohio) and fitted with a flat beater attachment. The mixture is vigorously aerated at high speed for 90 seconds to a wet foam density of approximately 0.19 grams/cm$^3$. The resulting aerated mixture is then spread with a spatula into molds made of high density polyethylene and with a rectangular shaped interior cavity of 150 mm length×87 mm width×5 mm depth and with a corrugated "wash board" pattern bottom surface consisting of reverse V-shaped rows raised by approximately 3 mm and with the trough of each row being evenly spaced every approximately 4.5 mm. A portion of the resulting aerated mixture is also spread with a spatula into circular Teflon molds with a 4.2 cm diameter and a depth of 0.6 cm for further structural measurements.

The segregated molds are then placed into a 75° C. convection oven for 30 minutes and then placed into a 40° C. convection oven for drying overnight. The following day, the resulting substrates are removed from the molds with the aid of a thin spatula and tweezers. The porous solids were weighed indicating approximate average dry densities of approximately 0.06 grams/cm$^3$ (360 grams per square meter basis weight). The estimated surfactant level is between 48 wt % and 64 wt % and the estimated polymer level is between 19% and 26%, assuming a moisture content of between 0 wt % and 10 wt %.

The below Table 2 give the structural and performance measurements taken on the resulting porous dissolvable solid substrate shampoo. SEM and micro-CT images were also taken and are referenced in the attached figures. The data was collected by the methods as described herein.

TABLE 2

| Example | Kr BET Surface Area (m²/g) | Pycnometry % Open Cells | Micro-CT Cell Wall thickness (mm) | Micro-CT Star Volume (mm³) | Micro-CT SMI Index | μCT Image | SEM Image |
|---|---|---|---|---|---|---|---|
| Ex. 1 | 0.056 | 96.5% | 0.112 | 43.6 | 2.3 | FIG. 5 | FIG. 6 |

The above data and referenced images demonstrate the porous dissolvable solid substrate shampoo of Example 1 to be predominantly open-celled and to have good physical integrity. Correspondingly, the porous dissolvable solid substrate exhibits fast dissolution performance and good lather volume (i.e. lather volume 65 ml and hand dissolution of 9 strokes) as measured by the methodologies as described herein.

Example 2

Self-Warming Porous Dissolvable Solid Substrate Shampoo Pouch Comprising a Surface Resident Powder Coating of Anhydrous Magnesium Sulfate in the Pouch Interior A portion of the porous dissolvable solid substrate from the corrugated molds of example 1 are cut with scissors into approximately 85 mm×43 mm rectangles with the corrugated surface facing down in a weigh boat. The weight of the cut substrate ranges from 0.8 to 0.9 grams. Approximately 2.4 grams of anhydrous $MgSO_4$ powder (available from Tomita Pharmaceutical Co., Ltd. Tokushima, Japan) is added to the central area of the exposed top surface of the substrate. A pouch is then prepared with the powder in the interior by carefully folding the substrate down the middle (without spillage of the powder) such that the two shortest sides meet together and with the three edges being lightly moistening with water with the aide of a moist polyurethane kitchen sponge and then pressing the edges together until a seal is formed.

A 25 ml glass beaker is filled with approximately 15 ml of luke-warm tap water at which is measured with a thermometer to be at approximately 30° C. An porous dissolvable solid substrate pouch comprising a surface resident coating of anhydrous magnesium sulfate is added to the water and made to dissolve by gentle stirring with the aide of a spatula. The water temperature quickly rises by 17° C. to a final reading of 47° C.

Example 3

Effervescent Porous Dissolvable Solid Substrate Shampoo Pouch Comprising a Surface Resident Powder Coating of a Blend of Citric Acid and Sodium Bicarbonate in the Pouch Interior An effervescent powder comprising sodium bicarbonate and citric acid is prepared with the use of a Flacktek Speemixer™ DAC400FV (By HAUSCHILD, Waterkamp 1, 509075 Hamm, Germany) and a two place weigh balance. 4.02 grams of sodium hydrogen carbonate (Catalog Number S6297 from Sigma Aldrich) and 4.16 grams of citric acid (Catalog Number 251275 from Sigma Aldrich) are weighed into a Flacktek Speedmixer 60 max jar. The jar is then sealed shut with the corresponding lid and speedmixed for approximately 35 seconds at 2750 rpm to finish the preparation of the effervescent powder.

A portion of the porous dissolvable solid substrate from the corrugated molds of example 1 are cut with scissors into approximately 2 inch×1.5 inch rectangles with the corrugated surface facing down in a weigh boat. The weight of the cut substrate ranges from 0.8 to about 1.0 grams. Approximately 2.3 grams of the above prepared effervescent powder comprising sodium bicarbonate and citric acid is added to the central area of the exposed top surface of the substrate. A pouch is then prepared with the powder in the interior by carefully folding the substrate down the middle (without spillage of the powder) such that the two shortest sides meet together and with the three edges being lightly moistening with water with the aide of a moist polyurethane kitchen sponge and then pressing the edges together until a seal is formed.

Two 50 ml glass graduated cylinders are each filled with approximately 12-14 ml of luke-warm tap water. Into the first graduated cylinder, 2.5 ml of a retail liquid shampoo control (Pantene Pro-V) is added to the water with the aide of a syringe and with gentle stirring with the aide of a spatula. Into the second graduated cylinder, a porous dissolvable solid substrate shampoo pouch comprising a surface resident coating of a powder blend of sodium bicarbonate and citric acid is added to the water and made to dissolve by gentle stirring with the aide of a spatula. While no gas bubbles is visibly produced in the first graduated cylinder, gas bubbles are immediately produced within the second cylinder and with the resulting foam rising beyond the rim of the graduated cylinder.

Example 4

Hair Bleaching Porous Dissolvable Solid Substrate Comprising Surface Resident Bleach Powder Coatings Four representative hair bleach powders were prepared by admixing the below dry ingredients followed by grinding to a fine powder within a small Black & Decker® coffee mill with repeated pulses spanning 2 to 3 minutes (approximately 10 grams per powder preparation). The representative bleach powders chosen all include sodium percarbonate in combination with either ammonium sulfate or ammonium persulfate and with optional glycine as a free radical scavenger (all chemicals available from Sigma-Aldrich, Milwaukee, Wis.). The powder compositions are given in Table 3 with all percentages being weight percentages of the total powder composition:

TABLE 3

|  | Sodium percarbonate | Ammonium sulfate | Ammonium persulfate | Glycine |
| --- | --- | --- | --- | --- |
| Ex. 4-1 | 56% | 33% | 0% | 9% |
| Ex. 4-2 | 63% | 37% | 0% | 0% |
| Ex. 4-3 | 55% | 32% | 0% | 13% |
| Ex. 4-4 | 48% | 0% | 52% | 0% |

To evaluate the influence of applied surface resident coatings of the above bleach powders onto the porous dissolvable solid substrate of example 1, it is assumed that approximately 2.3 grams of substrate (comprising approximately 60% by weight surfactant) would constitute a single dose for application to an average of 100 grams of hair (0.023 grams of dissolving porous shampoo solid per gram of hair). For testing purposes, the bleaching performance of each product is evaluated on two 7 inch long 1.5 gram virgin brown hair switches with a combined weight of 3 grams of hair. Therefore, the substrate dose is scaled down to approximately 0.07 grams (0.23 grams of solid shampoo per gram of hair) by cutting the substrates with scissors. The respective bleach powders are then applied to by carefully coating the exposed surfaces of the cut piece of substrate with approximately 0.2 grams of each respective powder. Base line L, a, b, c, h color readings are obtained on each of the hair switches employing a Minolta Spectrophotometer and averaged. For the evaluation, the two hair switches are hung together over a sink and wetted with 100° F. tap water flowing at a rate of 1.5 gallons per minute. For each bleach treatment, the cut substrate with surface adsorbed bleach powder is applied to the center of the combined switches and with 2 cm$^3$ of additional water being applied on top of the solid with a syringe to facilitate the solid dissolution. The switches are then lathered for 30 seconds by repeatedly rubbing and squeezing the hair switch with both hands in a downward motion. After a time period of 5 minutes, the switches are then thoroughly rinsed with the tap water for 30 seconds. A total of 14 of the above bleach treatments are performed with drying in-between each. L, a, b, c, h color readings are recorded after every two bleach treatments on each switch and averaged. The L, a, b, c, h values are given in the below tables and the L-values (indicative of melanin bleaching or hair lightening) can also be viewed graphically in FIG. 5.

TABLE 4

Hair Lightening Data (L, a, b, c, h values) For Ex. 1 Porous Dissolvable Solid Substrate Shampoo with Surface Resident Coating 4-1 (56% Sodium Percarbonate/33% Ammonium Sulfate/9% Glycine)

| Bleach Treatment | L-values (D65) | a-values (D65) | b-values (D65) | c-values (D65) | h-values (D65) |
| --- | --- | --- | --- | --- | --- |
| 0 | 25.17 | 4.78 | 6.83 | 8.34 | 55.01 |
| 2 | 25.17 | 4.80 | 6.74 | 8.28 | 54.55 |
| 4 | 25.77 | 4.82 | 6.80 | 8.33 | 54.65 |
| 6 | 25.75 | 5.22 | 7.59 | 9.21 | 55.49 |
| 8 | 26.09 | 5.47 | 7.65 | 9.40 | 54.44 |
| 10 | 26.06 | 5.15 | 7.27 | 8.91 | 54.70 |
| 12 | 26.65 | 5.65 | 8.29 | 10.03 | 55.76 |
| 14 | 26.45 | 5.67 | 8.18 | 9.95 | 55.27 |

TABLE 5

Hair Lightening Data (L, a, b, c, h values) For Ex. 1 Porous Shampoo Solid with Surface Resident Coating 4-2 (63% Sodium Percarbonate/37% Ammonium Sulfate)

| Bleach Treatment | L-values (D65) | a-values (D65) | b-values (D65) | c-values (D65) | h-values (D65) |
| --- | --- | --- | --- | --- | --- |
| 0 | 25.13 | 4.66 | 6.65 | 8.12 | 54.96 |
| 2 | 25.60 | 4.93 | 6.93 | 8.51 | 54.56 |
| 4 | 26.69 | 5.46 | 7.97 | 9.67 | 55.59 |
| 6 | 26.62 | 6.04 | 8.94 | 10.78 | 55.93 |
| 8 | 27.86 | 6.09 | 9.03 | 10.89 | 56.00 |
| 10 | 27.43 | 6.19 | 9.19 | 11.08 | 56.04 |
| 12 | 28.13 | 6.59 | 9.81 | 11.81 | 56.12 |
| 14 | 28.16 | 6.71 | 10.42 | 12.39 | 57.23 |

TABLE 6

Hair Lightening Data (L, a, b, c, h values) For Ex. 1 Porous Shampoo Solid with Surface Resident Coating 4-3 (55% Sodium Percarbonate/32% Ammonium Sulfate/13% Glycine)

| Bleach Treatment | L-values (D65) | a-values (D65) | b-values (D65) | c-values (D65) | h-values (D65) |
| --- | --- | --- | --- | --- | --- |
| 0 | 24.74 | 4.76 | 6.82 | 8.31 | 55.10 |
| 2 | 25.12 | 4.62 | 6.60 | 8.05 | 54.95 |
| 4 | 25.49 | 4.63 | 6.50 | 7.98 | 54.51 |
| 6 | 25.33 | 5.21 | 7.26 | 8.94 | 54.30 |
| 8 | 26.01 | 5.21 | 7.54 | 9.16 | 55.33 |
| 10 | 25.83 | 5.14 | 7.21 | 8.85 | 54.55 |
| 12 | 26.15 | 5.32 | 7.52 | 9.22 | 54.73 |
| 14 | 26.29 | 5.60 | 7.99 | 9.75 | 54.96 |

TABLE 7

Hair Lightening Data (L, a, b, c, h values) For Ex. 1 Porous Shampoo Solid with Surface Resident Coating 4-4 (48% Sodium Percarbonate/52% Ammonium Persulfate)

| Bleach Treatment | L-values (D65) | a-values (D65) | b-values (D65) | c-values (D65) | h-values (D65) |
| --- | --- | --- | --- | --- | --- |
| 0 | 24.69 | 4.61 | 6.45 | 7.93 | 54.44 |
| 2 | 25.56 | 4.84 | 6.85 | 8.39 | 54.71 |
| 4 | 26.22 | 5.29 | 7.60 | 9.26 | 55.13 |
| 6 | 26.39 | 6.10 | 8.98 | 10.85 | 55.83 |
| 8 | 27.33 | 5.92 | 8.61 | 10.45 | 55.46 |
| 10 | 27.65 | 6.24 | 9.27 | 11.17 | 56.07 |
| 12 | 28.85 | 6.77 | 10.65 | 12.61 | 57.57 |
| 14 | 27.89 | 7.06 | 10.60 | 12.73 | 56.34 |

Note that any actives and/or compositions disclosed herein can be used in and/or with the articles, and in particular the household care articles, disclosed in the following U.S. patent applications, including any publications claiming priority thereto: U.S. 61/229,981; U.S. 61/229,986; U.S. 61/229,990; U.S. 61/229,996; U.S. 61/230,000; and U.S. 61/230,004. Such articles may comprise one or more of the following: detersive surfactant; plasticizer; enzyme; suds suppressor; suds booster; bleach; bleach stabilizer; chelant; cleaning solvent; hydrotrope; divalent ion; fabric softener additive (e.g. quaternary ammonium compounds); nonionic surfactant; perfume; and/or a perfume delivery system. Such articles may be utilized in methods including, but not limited to: dosing into a washing machine to clean and/or treat fabric; dosing into a dishwasher to clean and/or treat cutlery; and dosing into water to clean and/or treat fabric and/or hard surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care article comprising:
   a.) a porous dissolvable solid substrate comprising:
      i. from about 10% to about 75% of a surfactant;
      ii. from about 10% to about 50% water-soluble polymer;
      iii. from about 1% to about 30% plasticizer; and
   b.) a surface resident coating comprising from about 10% to about 100% of one or more water sensitive actives;
   wherein the ratio of porous dissolvable solid substrate to the surface resident coating from about 110:1 to about 0.1:1;
   wherein the porous dissolvable solid substrate comprises a percent open cell content from about 80% to about 100.0%; and
   wherein said article has a solid density of from about 0.08 g/cm³ to about 0.30 g/cm³;
   and wherein the personal care article has a hand dissolution value of about 3 to about 20 strokes.

2. The personal care article of claim 1, wherein the water sensitive active is selected from oxidative bleaching and dyeing compounds, effervescent agents, warming agents; and color indicator agents.

3. The personal care article of claim 2, wherein the oxidative bleaching and dyeing compounds are selected from developer dye compounds, coupler dye compounds, oxidizing agents, chelants, pH modifiers and buffering agents, carbonate ion sources, radical scavenger systems, peroxide stabilizing agents and mixtures thereof.

4. The personal care article of claim 2, wherein the oxidizing bleaching and dyeing compound is selected from sodium percarbonate, ammonium carbonate, potassium percarbonate, sodium persulfate, ammonium persulfate, potassium persulfate, and mixtures thereof.

5. The personal care article of claim 2, wherein the water sensitive active is an effervescent agent is selected from a mixture comprising from about 10% to about 60% of an alkali metal salt and from about 10% to about 60% of an acid, both by weight of the effervescent.

6. The personal care article of claim 5, wherein the alkali metal salt is selected from sodium carbonate or sodium bicarbonate and the acid is selected from citric acid.

7. The personal care article of claim 2, wherein the water sensitive active is a warming agents selected from inorganic salts, glycols, finely divided solid adsorbent materials, iron redox systems and combinations thereof.

8. The personal care article of claim 7, wherein the inorganic salts are selected from anhydrous inorganic salts including calcium chloride, magnesium chloride, calcium oxide, magnesium sulphate, sodium sulphate, aluminum sulphate, and combinations thereof.

9. The personal care article of claim 8, wherein the anhydrous inorganic salts are selected from anhydrous calcium chloride and anhydrous magnesium sulphate, and mixtures thereof.

10. The personal care article of claim 2, wherein the water sensitive active is a color indicator agent is selected from pH indicators.

11. The personal care article of claim 10, wherein pH indicator is selected from the group consisting of bromocresol green, phenolphthalein, σ-cresolphthalein, thymolphthalein, coumarin, 2,3-dioxyxanthone, coumeric acid, 6,8-dinitro-2,4(1H) quinazolinedione, and ethyl-bis(2,4-dimethylphenyl) ethanoate.

12. The personal care article of claim 2, wherein the surfactant further comprises a Group II surfactant, wherein the Group II surfactant is selected from the group consisting of amphoteric surfactants, zwitterionic surfactants, and combinations thereof.

13. The personal care article of claim 1, wherein the Group I surfactant is an anionic surfactant selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

14. The personal care article of claim 1, wherein the surfactant is selected from the group consisting of (i) 0.1% to about 10% of an ionic surfactant, (ii) a non-ionic surfactant, (iii) a polymeric surfactant and (iv) any combination thereof.

15. The personal care article of claim 1, wherein the ratio of the porous dissolvable solid substrate to the surface resident coating is from about 20:1 to about 0.2:1.

16. The personal care article of claim 1, wherein the ratio of the porous dissolvable solid substrate to the surface resident coating is from about 10:1 to about 0.3:1.

17. The personal care article of claim 1, wherein the ratio of the porous dissolvable solid substrate to the surface resident coating is from about 1:1 to about 0.4:1.

18. The personal care article of claim 1, wherein the surface resident coating comprising the water sensitive active is a powder.

19. The personal care article of claim 1, wherein the surface resident coating comprising the water sensitive active is attached to at least a portion of an outer surface of the porous dissolvable solid substrate.

20. The personal care article of claim 1, wherein the surface resident coating comprising the water sensitive active covers an outer surface of the porous dissolvable solid substrate.

21. The personal care article of claim 1, wherein the personal care article comprises two porous dissolvable solid substrates, and wherein the surface resident coating comprising the water sensitive active is a layer situated between the two porous dissolvable solid substrates.

22. The personal care article of claim 1, wherein the porous dissolvable solid substrate is folded over and the surface resident coating comprising the water sensitive active is enclosed within the porous dissolvable solid substrate.

23. The personal care article of claim 1, the porous dissolvable solid substrate having a basis weight of from about 125 grams/m² to about 3,000 grams/m² and a thickness of from about 0.5 mm to about 10 mm.

24. The personal care article of claim 1, wherein the porous dissolvable solid substrate comprises a specific surface area from about 0.03 m²/gram to about 0.25 m²/gram.

25. The personal care article of claim 1, wherein the porous dissolvable solid substrate comprises a cell wall thickness of from about 0.02 mm to about 0.15 mm.

* * * * *